US010426656B2

(12) United States Patent
Taylor

(10) Patent No.: US 10,426,656 B2
(45) Date of Patent: Oct. 1, 2019

(54) THERMAL CONTROL SYSTEM

(71) Applicant: Stryker Corporation, Kalamazoo, MI (US)

(72) Inventor: Gregory S. Taylor, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/646,847

(22) Filed: Jul. 11, 2017

(65) Prior Publication Data
US 2018/0014967 A1    Jan. 18, 2018

Related U.S. Application Data

(60) Provisional application No. 62/361,124, filed on Jul. 12, 2016.

(51) Int. Cl.
*A61F 7/00* (2006.01)
*A61F 7/02* (2006.01)

(52) U.S. Cl.
CPC .............. *A61F 7/0085* (2013.01); *A61F 7/02* (2013.01); *A61F 2007/0054* (2013.01); *A61F 2007/0096* (2013.01)

(58) Field of Classification Search
CPC .......... B01D 19/0042; A61F 7/00; A61F 7/02; A61F 7/0085; A61F 2007/0054; A61F 2007/0096
See application file for complete search history.

(56) References Cited

U.S. PATENT DOCUMENTS

| 4,118,946 | A | 10/1978 | Tubin |
|---|---|---|---|
| 5,172,511 | A | 12/1992 | Smith et al. |
| 5,482,355 | A | 1/1996 | Franzen, Jr. |
| 5,486,206 | A | 1/1996 | Avery |
| 5,647,051 | A | 7/1997 | Neer |
| 5,845,501 | A | 12/1998 | Stonehouse et al. |
| 5,948,012 | A | 9/1999 | Mahaffey et al. |
| 6,197,045 | B1 | 3/2001 | Carson |

(Continued)

OTHER PUBLICATIONS

Sorin Group, Heater-Cooling System 3T, Operating Instructions, Feb. 2015.

(Continued)

*Primary Examiner* — Keith M Raymond
*Assistant Examiner* — Gordon A Jones
(74) *Attorney, Agent, or Firm* — Warner Norcross + Judd LLP

(57) ABSTRACT

A thermal control unit for delivering temperature-controlled fluid to one or more patient therapy devices (e.g. pads, blankets, etc.) that are in contact with a patient is disclosed. The thermal control unit includes a fluid circuit with an inlet and outlet, a reservoir, a heat exchanger, a pump, and a controller. The thermal control also includes any one or more of the following: (1) an air eliminator with an air filter for filtering air vented from the fluid circuit to the ambient surroundings; (2) a plug that moves in response to changing fluid levels and that fluidly isolates the air filter from the fluid; (3) a second air filter coupled to the reservoir; (4) a check valve to prevent fluid from back flowing into the reservoir; and/or (5) a liquid filter coupleable to the reservoir to filter liquid entering or exiting the reservoir.

14 Claims, 6 Drawing Sheets

(56) References Cited

U.S. PATENT DOCUMENTS

| | | | |
|---|---|---|---|
| 6,214,096 B1* | 4/2001 | Kwak | B01D 19/0042 96/165 |
| 6,371,976 B1 | 4/2002 | Vrzalik et al. | |
| 6,620,187 B2 | 9/2003 | Carson et al. | |
| 6,692,518 B2 | 2/2004 | Carson | |
| 6,699,266 B2 | 3/2004 | Lachenbruch et al. | |
| 6,699,267 B2 | 3/2004 | Voorhees et al. | |
| 6,818,012 B2 | 11/2004 | Ellingboe | |
| 6,878,156 B1 | 4/2005 | Noda | |
| 7,008,445 B2 | 3/2006 | Lennox | |
| 7,106,662 B1 | 9/2006 | Acker, Jr. | |
| 7,481,238 B2 | 1/2009 | Ramoth | |
| 7,972,287 B2 | 7/2011 | Stewart et al. | |
| 8,512,263 B2 | 8/2013 | Gammons | |
| 8,657,864 B2 | 2/2014 | Rein et al. | |
| 8,801,272 B2 | 8/2014 | Bieberich et al. | |
| 8,968,378 B2 | 3/2015 | Ginsburg et al. | |
| 9,504,601 B1* | 11/2016 | Lewis | A61F 7/0097 |
| 2003/0078638 A1* | 4/2003 | Voorhees | A61F 7/0085 607/104 |
| 2003/0114903 A1 | 6/2003 | Ellingboe | |
| 2004/0210283 A1 | 10/2004 | Rose et al. | |
| 2005/0081716 A1* | 4/2005 | Morita | B01D 19/0042 95/241 |
| 2006/0005314 A1 | 1/2006 | Lee | |
| 2007/0288074 A1 | 12/2007 | Cazzini | |
| 2008/0060374 A1 | 3/2008 | Gammons et al. | |
| 2008/0255644 A1 | 10/2008 | Carson | |
| 2010/0076531 A1 | 3/2010 | Beran et al. | |
| 2010/0107878 A1* | 5/2010 | Crowder | B01D 19/0031 96/6 |
| 2010/0274331 A1 | 10/2010 | Williamson et al. | |
| 2010/0316534 A1* | 12/2010 | Niazi | A61L 9/145 422/122 |
| 2013/0085552 A1 | 4/2013 | Mandel | |
| 2013/0098069 A1 | 4/2013 | Collins | |
| 2013/0158443 A1 | 6/2013 | Kraal et al. | |
| 2014/0174070 A1* | 6/2014 | Olateru | F15B 21/044 60/453 |
| 2014/0222121 A1 | 8/2014 | Spence et al. | |
| 2014/0243939 A1* | 8/2014 | Lowe | A61F 7/02 607/104 |
| 2014/0265502 A1 | 9/2014 | Hough et al. | |
| 2014/0343639 A1* | 11/2014 | Hopper | A61F 7/0085 607/104 |
| 2015/0366367 A1 | 12/2015 | Augustine et al. | |
| 2016/0114275 A1* | 4/2016 | Schwartz | B01D 46/0024 55/488 |
| 2016/0140307 A1 | 5/2016 | Brosnan et al. | |

OTHER PUBLICATIONS

Medivance, Arctic Sun 5000, Service Manual, (2010-2011).
Altrix Precision Temperature Management System Stryker Operations Manual, Dec. 2016.
Honeywell Braukmann EA122A Automatic Air Vent Operations Manual, Feb. 1993.
Gaymar Medi-Therm III, Hyper/Hypothermia Machine Ref MTA7912 Service Manual, Nov. 2009.
Copending Provisional Application and Drawings U.S. Appl. No. 62/344,779, filed Jun. 2, 2016.
International Search Report and Written Opinion for PCT/US2017/041510, the international counterpart to U.S. Appl. No. 15/646,847.
Stryker Air Pump 2861 Operation/Maintenance Manual, Jun. 2016.
Stryker Sage Products Prevalon Air Pump Brochure, 2017.
Taco Submittal Data Information Automatic Air Vents Brochure, effective Jun. 1, 2010.

* cited by examiner

THERMAL CONTROL SYSTEM

CROSS-REFERENCE TO RELATED APPLICATIONS

This application claims priority to U.S. provisional patent application Ser. No. 62/361,124 filed Jul. 12, 2016, by inventor Gregory Taylor and entitled THERMAL CONTROL SYSTEM, the complete disclosure of which is incorporated herein by reference.

BACKGROUND

The present disclosure relates to a thermal control system for controlling the temperature of circulating fluid which is delivered to one or more thermal pads positioned in contact with a patient.

Thermal control systems are known in the art for controlling the temperature of a patient by supplying temperature-controlled fluid to one or more pads, blankets, or similar structures, that are positioned in contact with, or adjacent to, a patient. The temperature of the fluid is controlled by a thermal unit that provides fluid to the pads or blankets. After passing through the pads or blankets, the fluid is returned to the control unit where any necessary adjustments to the returning fluid temperature are made before being pumped back to the pad or blanket. In some instances, the temperature of the fluid is controlled to a target fluid temperature, while in other instances the temperature of the fluid is controlled in order to effectuate a target patient temperature. When controlling a patient's temperature, a patient temperature probe may be attached to the control unit in order to provide patient temperature readings as feedback to the control unit so that it can make the necessary temperature adjustments to the circulating fluid.

SUMMARY

The present disclosure provides various improved aspects to a thermal control system. In one embodiment, the present disclosure includes a thermal control unit that substantially prevents the escape of aerosolized fluid contained within the thermal control unit and used to control the temperature of the patient. In one or more embodiments, the present disclosure includes a thermal control unit that helps prevent spillage of the fluid used to control the temperature of the patient, such as spillage due to back flow of the fluid into a reservoir in the thermal control unit. In one or more embodiments, the present disclosure includes a thermal control unit that facilitates the use of clean fluid in the thermal control unit.

According to one embodiment, a thermal control unit is provided that includes a fluid circuit, a reservoir, a heat exchanger, a pump, an air eliminator, an air filter, and a controller. The fluid circuit includes a fluid outlet adapted to couple to a fluid supply line and a fluid inlet adapted to couple to a fluid return line. The reservoir supplies fluid to the fluid circuit. The heat exchanger changes a temperature of the fluid in the fluid circuit. The pump circulates the fluid supplied by the reservoir through the fluid circuit. The air eliminator vents air from the fluid circuit to the ambient surroundings. The controller controls the heat exchanger such that a temperature of the circulating fluid is adjusted toward a desired temperature. And the air filter couples to the air eliminator and filters the air vented to the ambient surroundings by the air eliminator.

According to another embodiment, a thermal control unit is provided that includes a fluid circuit, a reservoir, a heat exchanger, a pump, an air eliminator, an air filter, a plug, and a controller. The fluid circuit includes a fluid outlet adapted to couple to a fluid supply line and a fluid inlet adapted to couple to a fluid return line. The reservoir supplies fluid to the fluid circuit. The heat exchanger changes a temperature of the fluid in the fluid circuit. The pump circulates the fluid supplied by the reservoir through the fluid circuit. The air eliminator vents air from the fluid circuit to the ambient surroundings. The plug has a position that varies in response to a level of fluid in the thermal control unit. The plug is adapted to fluidly isolate the air filter from the fluid in the thermal control unit if the level of fluid in the thermal control unit exceeds a threshold. The controller controls the heat exchanger such that a temperature of the circulating fluid is adjusted toward a desired temperature.

According to another embodiment, a thermal control unit is provided that includes a fluid circuit, a removable reservoir, a heat exchanger, a pump, an air eliminator, a check valve, and a controller. The fluid circuit includes a fluid outlet adapted to couple to a fluid supply line and a fluid inlet adapted to couple to a fluid return line. The reservoir supplies fluid to the fluid circuit. The heat exchanger changes a temperature of the fluid in the fluid circuit. The pump circulates the fluid supplied by the reservoir through the fluid circuit. The air eliminator vents air from the fluid circuit to the ambient surroundings. The check valve is positioned between the removable reservoir and the fluid circuit and is adapted to prevent fluid from flowing out of the fluid circuit and into the removable reservoir. The controller controls the heat exchanger such that a temperature of the circulating fluid is adjusted toward a desired temperature.

According to another embodiment, a thermal control unit is provided that includes a fluid circuit, a reservoir, a heat exchanger, a pump, and a controller. The fluid circuit includes a fluid outlet adapted to couple to a fluid supply line and a fluid inlet adapted to couple to a fluid return line. The reservoir supplies fluid to the fluid circuit and includes an air filter in fluid communication with an interior of the reservoir. The air filter filters air escaping from the interior of the reservoir. The heat exchanger changes a temperature of the fluid in the fluid circuit. The pump circulates the fluid supplied by the reservoir through the fluid circuit, and the controller controls the heat exchanger such that a temperature of the circulating fluid is adjusted toward a desired temperature.

According to still another embodiment, a thermal control unit is provided that includes a fluid circuit, a reservoir, a heat exchanger, a pump, and a controller. The fluid circuit includes a fluid outlet adapted to couple to a fluid supply line and a fluid inlet adapted to couple to a fluid return line. The reservoir supplies fluid to the fluid circuit and includes a liquid filter in fluid communication with an interior of the reservoir. The liquid filter filters the fluid when the fluid is poured into the reservoir. The heat exchanger changes a temperature of the fluid in the fluid circuit. The pump circulates the fluid supplied by the reservoir through the fluid circuit, and the controller controls the heat exchanger such that a temperature of the circulating fluid is adjusted toward a desired temperature.

According to other aspects, the plug sealingly engages an aperture when the plug rises past a threshold height, wherein the aperture is positioned between the air filter and the fluid.

In some embodiments, one or two air filters are included that have pore sizes no greater than 0.2 microns.

The reservoir is adapted to be lifted out of the thermal control unit without leaking fluid, in at least some embodiments.

An air and liquid filter is included in some embodiments that is adapted to filter the fluid when the fluid is poured into the removable reservoir and to filter air escaping from the removable reservoir to the ambient surroundings. The air and liquid filter may be integrated into a removable lid adapted to be selectively attached to, and detached from, the removable reservoir.

According to another embodiment, a thermal control unit is provided that includes a fluid circuit, a heat exchanger, a pump, and a controller. The fluid circuit includes a fluid outlet adapted to couple to a fluid supply line and a fluid inlet adapted to couple to a fluid return line. The heat exchanger is adapted to change a temperature of fluid in the fluid circuit. The pump circulates fluid through the fluid circuit. The controller communicates with a disinfection unit and controls the pump in order to pump disinfecting fluid through the fluid circuit. The controller also controls a drain to drain the disinfecting fluid from the fluid circuit based upon communication received from the disinfection unit.

According to other aspects, the controller controls the pump such that the disinfecting fluid flows through the fluid circuit for a predetermined amount of time before draining the disinfecting fluid and/or controls the heat exchanger such that a temperature of the disinfecting fluid is controlled toward a target temperature while flowing through the fluid circuit.

In some embodiments, the thermal control unit is adapted to receive the disinfecting fluid via the fluid inlet and to drain the disinfecting fluid via the fluid outlet.

The controller is further adapted to control the pump and the heat exchanger in order to deliver temperature-controlled non-disinfecting fluid to a thermal pad via the fluid outlet and to receive the temperature-controlled non-disinfecting fluid back from the thermal pad via the fluid inlet.

In some embodiments, a drain valve is also included that is in communication with the controller. The controller drains the disinfecting fluid by opening the drain valve.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
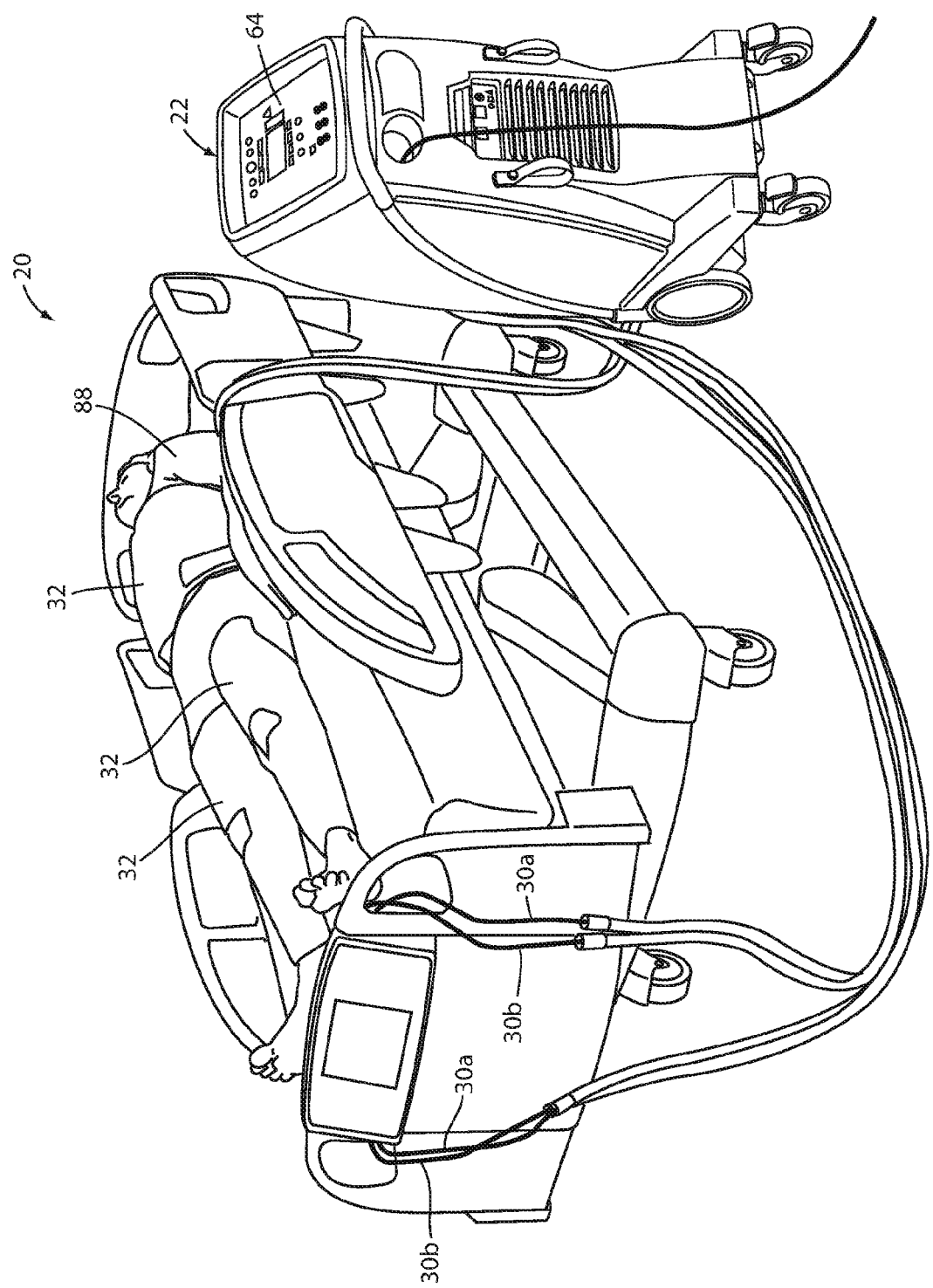
FIG. 1 is a perspective view of a thermal control system that may be used to provide thermal treatment to a patient.

A thermal control system 20 according to one embodiment of the present disclosure is shown in FIG. 1. Thermal control system 20 includes a thermal control unit 22 coupled to one or more thermal therapy devices 32. The thermal therapy devices 32 are wrapped around different portions of a patient 88, such as, but not limited to, the patient's torso and legs. The thermal control unit 22 delivers temperature controlled fluid to the thermal therapy devices 32 in order to control a temperature of the patient.

Figure 2:
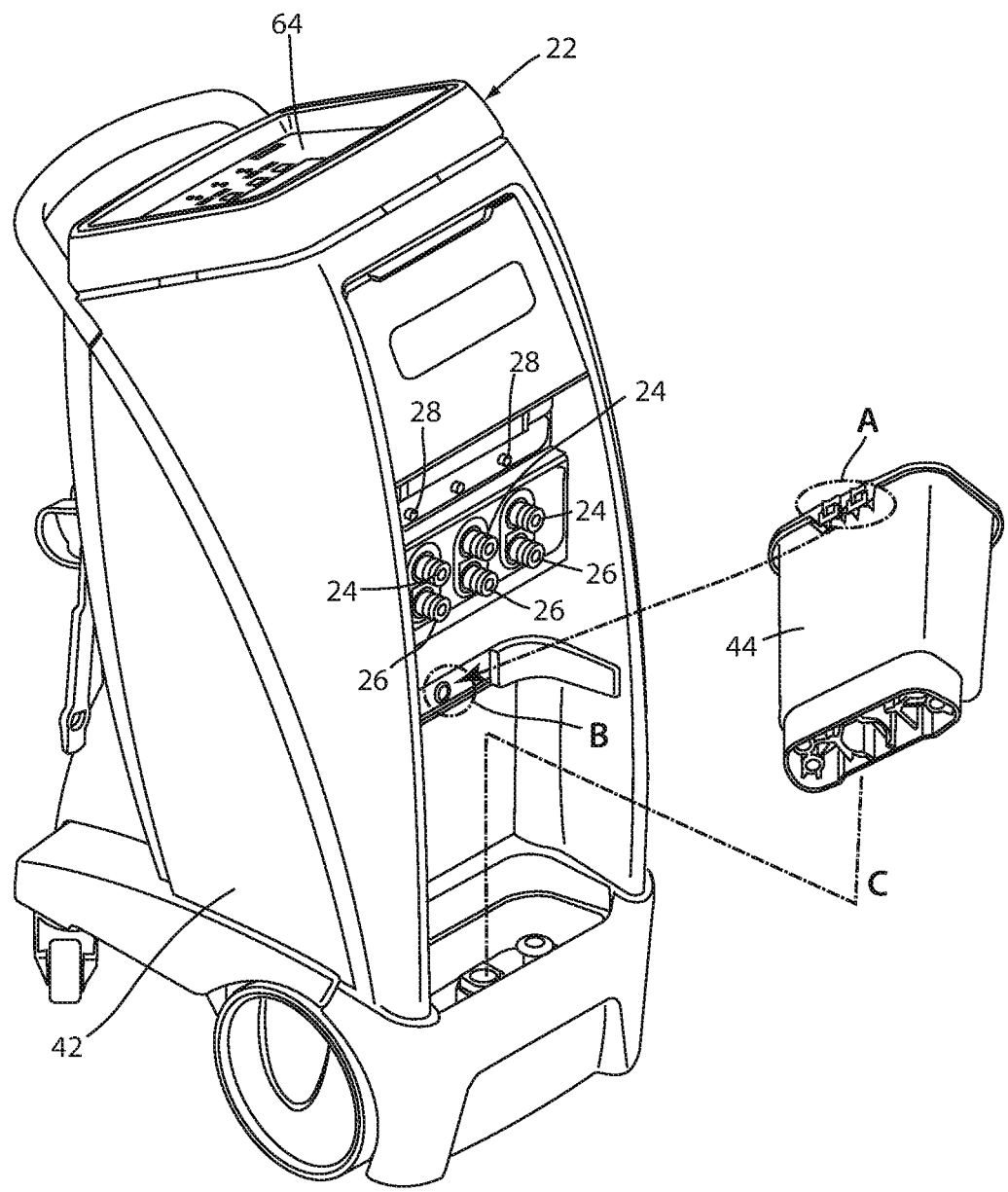
FIG. 2 is a perspective view of a thermal control unit of the thermal control system of FIG. 1.
Figure 3:
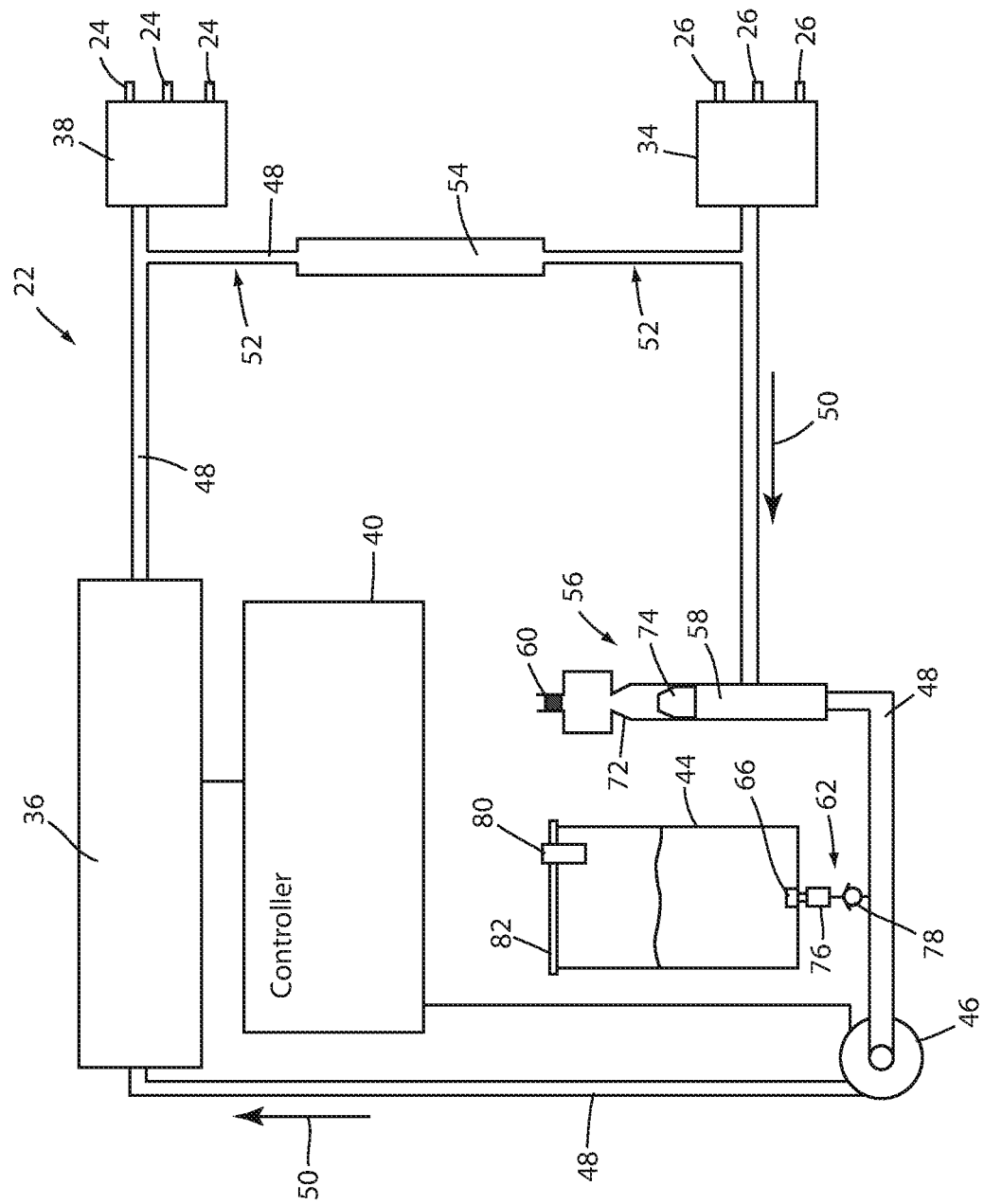
FIG. 3 is block diagram of the thermal control unit of FIG. 2.

Thermal control unit 22 includes a plurality of fluid outlet ports 24, a plurality of fluid inlet ports 26, and a plurality of patient temperature probe ports 28 (FIGS. 2-3). The outlet ports 24 are each adapted to be fluidly coupled to a corresponding fluid supply line or hose 30a (FIG. 1) that transports a thermal fluid from the thermal control unit 22 to a connected patient thermal therapy device 32, which may be a pad, a blanket, a vest, or other structure. For purposes of the following written description, thermal therapy device 32 will be referred to as a thermal pad 32, but it will be understood by those skilled in the art that thermal pad 32 is not limited to pads, but includes other types of patient thermal therapy devices. The inlet ports 26 define fluid inlets into control unit 22 and are each adapted to be fluidly coupled to a corresponding fluid return line or hose 30b that returns the thermal fluid from the thermal pad 32 back to the control unit 22. The fluid inside of control unit 22 is therefore pumped by control unit 22 in a circuit that starts at control unit 22, continues through supply lines 30a to the thermal pads 32, and returns back to the control unit 22 by way of return lines 30b.

Thermal control unit 22 of FIGS. 1-3 circulates the fluid through three fluid circuits. Each fluid circuit is defined by control unit 22, one of the connected thermal pads 32, and the corresponding pair of supply and return lines 30a and 30b. In the embodiment shown in FIGS. 1-3, the fluid that returns to control unit 22 from each return line 30b is mixed in a common return or inlet manifold 34, and the temperature of that mixed fluid is controlled to a single desired temperature (which may vary, as will be described more below) by passing it through a heat exchanger 36 (described below). The temperature-controlled fluid is then pumped to an outlet manifold 38 having three outlet ports 24 for delivery to each supply line 30a, so that the temperature of the fluid delivered to each outlet port 24 is the same. In this embodiment, each fluid circuit is supplied with fluid at outlet ports 24 that is at the same temperature. In an alternative embodiment, control unit 22 is configured to be able to maintain temperature isolation between one or more of the fluid circuits so that fluid of differing temperatures may be delivered from control unit 22 to the outlet ports 24, and thereafter to the thermal pads 32.

By coupling a supply line 30a to each of these three outlet ports 24 and a return line 30b to each of these three inlet ports 26 of thermal control unit 22, temperature controlled fluid can be delivered from control unit 22 to three different thermal pads 32. It will be understood by those skilled in the art that the number of ports 24 and 26 can be varied to include either a smaller or a greater number than the three illustrated in FIGS. 1-3. Still further, it will be understood by those skilled in the art that the ports 24, 26 may be provided in various physical configuration and combinations to facilitate the connection and disconnection of the lines 30a, 30b and/or thermal pads 32. As but one example, instead of using a separate pair of ports 24 and 26 for each individual fluid circuit, it is possible to modify control unit 22 to include a single multi-tube outlet port 24 and a single multi-tube inlet port 26 that simultaneously couples and de-couples multiple sets of supply lines 30a and return lines 30b to and from control unit 22. Still other variations are possible.

Thermal pads 32 may be any pad, blanket, or other structure adapted to be positioned in either direct contact or close contact with a patient 88. By controlling the temperature of the fluid flowing through hoses 30 to thermal pads 32, the temperature of a patient can be controlled via the close contact of the pads 32 with the patient and the resultant heat transfer therebetween. In one conventional configuration illustrated in FIG. 1, a first thermal pad 32 is wrapped around a patient's torso, while second and third thermal pads 32 are wrapped, respectively, around the patient's right and left legs. Other configurations can be used and, as noted, different numbers of thermal pads 32 may be used with thermal control unit 22, depending upon the number of inlet and outlet ports 26 and 24 that are included with thermal control unit 22. Still further, in some embodiments of thermal control system 20, one or more branching connectors (not shown) may be coupled to a single pair of inlet and outlet ports 26 and 24, if desired, so that multiple lines 30 and multiple thermal pads 32 may be supplied via a single inlet/outlet pair.

Thermal control system 20 also includes, in some embodiments, a plurality of patient temperature probes that are attached to a plurality of different locations of thermal interest on a patient. Such patient temperature probes may be any suitable patient temperature probe that is able to sense the temperature of the patient at the location of the probe. In one embodiment, the patient temperature probes are conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in system 20, each temperature probe is connected to a patient temperature probe port 28 positioned on control unit 22. Patient temperature probe ports 28 are in electrical communication with a controller 40 (FIG. 3) that is adapted, in at least some situations, to use the temperature sensed by at least one of the probes in controlling the temperature of the fluid circulated through control unit 22 and pads 32.

Thermal control unit 22 is adapted, in the illustrated embodiment, to operate in a plurality of different modes that are selectable by a user. In a first mode, known as a manual mode, the thermal control unit 22 controls the temperature of the liquid circulating through control unit 22—and thereby the temperature of the fluid delivered to thermal pads 32—so that it matches a target temperature chosen by the user. In this mode, the control unit 22 maintains the liquid at the chosen target temperature regardless of the patient's temperature. Indeed, in the manual mode, control unit 22 may be used without any patient temperature probes. In a second mode, known as an automatic mode, the thermal control unit 22 controls the temperature of the liquid circulating through control unit 22 in such a manner that a target patient temperature is achieved and/or maintained. In this automatic mode, at least one patient temperature probe must be coupled to control unit 22 so that control unit 22 knows the patient's current temperature. In the automatic mode, control unit 22 does not necessarily adjust the temperature of the circulating fluid to maintain a constant temperature, but instead makes the necessary temperature adjustments to the fluid in order to effectuate the desired patient temperature.

As shown more clearly in FIG. 2, thermal control unit 22 includes a main body 42 to which a removable reservoir 44 is able to be coupled and uncoupled. Removable reservoir 44 is configured to hold the fluid (typically water, although other liquids may be used) that is to be circulated through control unit 22 and the one or more thermal pads 32. By being removable from thermal control unit 22, reservoir 44 can be easily carried to a sink or faucet for filling and or dumping of the water or other fluid. This allows users of system 20 to more easily fill control unit 22 prior to its use, as well as to drain thermal control unit 22 after use. Removable reservoir 44 may further include volume gradations on its outside that provide a visual indication to the user of how much fluid is contained within reservoir 44. The individual gradations may correspond to any appropriate measure of fluid volume, such as, but not limited to, liters, gallons, quarts, fractions thereof, or any other units of fluid volume.

As shown more clearly in FIG. 3, thermal control unit 22 includes a pump 46 for circulating fluid through a circulation channel 48. Pump 46, when activated, circulates the fluid through circulation channel 48 in the direction of arrows 50 (clockwise in FIG. 3). Starting at pump 46, the circulating fluid first passes through heat exchanger 36 where it is delivered to outlet manifold 38 and its plurality of outlet ports 24. A bypass line 52 is fluidly coupled to outlet manifold 38 and inlet manifold 34. Bypass line 52 allows fluid to circulate through circulation channel 48 even in the absence of any thermal pads 32 or lines 30 being coupled to any of outlet and inlet ports 24 and 26. In the illustrated embodiment, bypass line 52 includes an optional filter 54 that is adapted to filter the circulating fluid. If included, filter 54 may be a particle filter adapted to filter out particles within the circulating fluid that exceed a size threshold, or filter 54 may be a biological filter adapted to purify or sanitize the circulating fluid, or it may be a combination of both.

Inlet manifold 34 includes the plurality of inlet ports 26 that receive fluid returning from the one or more connected thermal pads 32. The incoming fluid from inlet ports 26, as well as the fluid passing through bypass line 52, travels back toward the pump 46 into an air separator 56. Air separator 56 includes any structure in which the flow of fluid slows down sufficiently to allow air bubbles contained within the circulating fluid to float upward into a generally vertical tube 58 having an air filter 60 at its top end that is exposed to atmospheric pressure. Any air bubbles that are entrained in the circulating fluid will naturally rise up through vertical tube 58 of air separator 56, pass through air filter 60, and be vented to the atmosphere. Further details of air separator 56 are provided below with reference to FIG. 4. After passing through air separator 56, the circulating fluid flows past a valve array 62 positioned beneath fluid reservoir 44 and back to pump 46. Valve array 62 is described in greater detail below.

Thermal control unit 22 further includes controller 40 (FIG. 3). Controller 40 is contained within main body 42 and in electrical communication with a variety of different sensors and/or actuators. More specifically, controller 40 is in electrical communication with pump 46, heat exchanger 36, a control panel 64 (FIG. 1), and one or more temperature sensors that measure the temperature of the circulating fluid. Control panel 64 allows a user to operate thermal control unit 22, including setting a desired fluid target temperature and/or a desired patient target temperature, and/or to control other aspects of thermal control unit 22. The temperature sensors provide feedback to controller 40 that enables controller 40 to adjust heat exchanger 36, as appropriate, in order to effectuate closed-loop control of the temperature of the circulating fluid.

Controller 40 includes any and all electrical circuitry and components necessary to carry out the functions and algorithms described herein, as would be known to one of ordinary skill in the art. Generally speaking, controller 40 may include one or more microcontrollers, microprocessors, and/or other programmable electronics that are programmed to carry out the functions described herein. It will be understood that controller 40 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

Controller 40 uses the outputs of the one or more temperature sensors to control the temperature of the circulating fluid such that the circulating fluid has its temperature adjusted (or maintained) in accordance with the operating mode (manual or automatic) selected by the user of thermal control unit 22. Controller 40 may control the temperature of the fluid using a closed loop proportional-integral (PI) controller, a closed-loop proportional-integral-derivative (PID), controller, or some other type of closed-loop controller.

Further details regarding the construction and operation of thermal control unit 22 that are not described herein are found in commonly assigned U.S. patent application Ser. No. 14/282,383 filed May 20, 2014, inventors Christopher Hopper et al. and entitled THERMAL CONTROL SYSTEM, the complete disclosure of which is incorporated herein by reference.

Removable reservoir 44 includes a valve 66 on its bottom (FIG. 3) that automatically cooperates with a valve 76 within control unit 22 when reservoir 44 is inserted into thermal control unit 22. Valves 66 and 76 may be commercially available valves, such as are available from Colder Products Company of St. Paul, Minn., or from other suppliers. Both valves 66 and 76 automatically close when reservoir 44 is removed from control unit 22 so that any fluid that is contained within reservoir 44 will not leak out of reservoir 44, and any fluid in the control unit 22 will not leak out of control unit 22. Valve 76 is part of the valve array 62 of thermal control unit 22. When removable reservoir 44 is inserted into control unit 22, valves 66 and 76 cooperate with each other to both open. This automatic opening allows fluid within reservoir 44 to flow into control unit 22, depending upon what fluid, if any, is already present within control unit 22 and the relative pressure of that fluid compared to any fluid that is contained within reservoir 44.

Generally speaking, a small amount of fluid will flow out of reservoir 44 and into thermal control unit 22 when reservoir 44 is initially connected to thermal control unit 22 and pump 46 is not turned on. This initial flow is due to gravity and will continue until the height of the fluid in reservoir 44 approximately matches the height of the fluid in thermal control unit 22. When the heights approximately match, the fluid pressures inside the reservoir and thermal control unit 22 balance and flow stops. When pump 46 is turned on, the fluid inside circulation channel 48 is pumped out of thermal control unit 22 into one or more connected thermal pads 32. As this fluid is pumped out, it is replaced by fluid from within reservoir 44, which flows into circulation channel 48. Reservoir 44 continues to replace the pumped fluid until the fluid returns to inlet manifold 34 and circulating channel 48 is completely filled with fluid (as well as the connected thermal pads 32). At that point, no more fluid flows out of reservoir 44.

Figure 4:
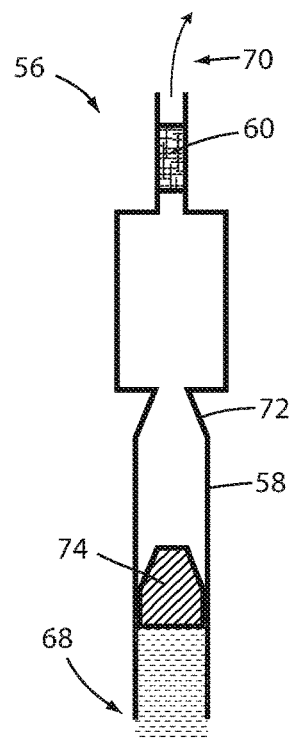
FIG. 4 is a side, elevation view of an air extraction unit of the thermal control unit of FIG. 2.

When pump 46 is initially turned on and fluid from reservoir 44 begins to fill the entirety of circulation channel 48, fluid lines 30a and 30b, as well as thermal pad(s) 32, the air that previously occupied these structures is vented to atmosphere via air separator 56 (FIGS. 3 and 4). Air separator 56 is shown in more detail in FIG. 4. As noted previously, air separator 56 includes a generally vertical tube 58 having a lower end 68 and an upper end 70. Vertical tube 58 includes a restricted region 72 positioned between upper end 70 and lower end 68. Inside of vertical tube 58 is a floating plug 74 that floats at different heights inside of vertical tube 58 depending upon the level of fluid and/or fluid pressure inside of thermal control unit 22. In some embodiments, the fluid level and pressure is such that plug 74 floats below constricted region 72 during normal operation of the thermal control unit 22. In other embodiments, plug 74 may be urged into contact with constricted region 72 during normal operation, but still allow bubbles to escape by temporarily dropping out of sealing contact with constricted region 72 when a bubble rises up vertical tube 58. In such embodiments, plug 74 allows one or more bubbles to escape while re-engaging constricted region 72 after the escape of such bubbles to thereby prevent liquid from flowing out the top of vertical tube 58.

However, when pump 46 is turned off, any fluid that is contained within thermal pads 32, fluid lines 30a and 30b, and/or the upper regions of circulation channel 48 will be pulled downward due to gravity toward the lower regions of circulating channel 48. This back flowing of fluid into control unit 22 causes the fluid level within vertical tube 58 to rise. This rising fluid level similarly causes the height of plug 74 to rise. If the back flow of fluid continues sufficiently, plug 74 eventually rises until it reaches constricted region 72. As can be seen in FIG. 4, restricted region 72 has an internal shape that generally matches an upper, external shape of plug 74. The continued rising of plug 74 therefore urges plug 74 into contact with restricted region 72 and creates a seal that prevents further filling of vertical tube 58 with fluid. This prevents fluid from ever rising high enough to escape out of upper end 70 of vertical tube 58 where it would otherwise spill onto the floor.

The sealing engagement of plug 74 with restricted region 72 also prevents fluid from ever rising in vertical tube 58 to a level where the fluid contacts air filter 60. This helps ensure that air filter 60 remains dry, which is generally advantageous in ensuring optimum efficiency of air filter 60. As shown in FIG. 4, air filter 60 is positioned vertically above constricted region 72. Air filter 60 is open to atmosphere at its top end and allows air inside of vertical tube 58 (which comes from within circulation channel 48, hoses 30, and pads 32 when they are initially being filled with liquid that forces out the air inside of them) to escape to atmosphere after passing therethrough. Air filter 60 is, in at least one embodiment, a High-Efficient Particulate Arresting (HEPA) air filter. Such air filters have pores sized to remove 99.97% of all particles having a size of 0.3 microns or greater.

In another embodiment, air filter 60 is an Ultra Low Penetration Air (ULPA) filter. Such filters are designed to remove 99.999% of particulates having a size of 0.1 microns or larger. Air filter 60 may also take on other designs. In some embodiments, air filter 60 is any air filter that is designed to remove particulates greater than or equal to 0.2 microns. Such filters substantially prevent bacteria or pathogens, such as, but not limited to, mycobacteria, that may have aerosolized inside of the fluid circuits of thermal control unit 22 from escaping into the surrounding environment. Air filter 60 therefore helps ensure that any pathogens contained with thermal control unit 22, hoses 30, and/or thermal pads 32, remain inside of control unit 22 and do not escape into the ambient surroundings where they could come into contact with patient 88 or other people.

In the embodiment shown in FIGS. 3-4, plug 74 floats in the fluid and makes direct sealing contact with constricted region 72. In another embodiment, plug 74 does not float directly in the fluid, but rather is mechanically coupled to a float that rises or falls with the rising or falling fluid level. The mechanical coupling selectively moves the plug 74 into sealing engagement with a constricted region. When the float is high enough, plug 74 therefore seals off any fluid flow (air or gas) from escaping out of the top end of the air separator. In one of these embodiments, plug 74 is incorporated into a Honeywell Braukmann EA122a Automatic Air Vent marketed by Honeywell Corporation of Golden Valley, Minn. In this embodiment, air filter 60 is coupled atop the Honeywell air vent such that air vented out of the Honeywell air vent must first pass through air filter 60 before being vented to the surrounding atmosphere. Other types of plugs 74 besides the Honeywell air vent may be used that do not directly float in the liquid.

As is also shown in FIG. 3, thermal control unit 22 also includes a check valve 78 as part of valve array 62. Check valve 78 is positioned between circulation channel 48 and reservoir 44. Check valve 78 is a one-way valve that substantially prevents fluid from flowing out of channel 48 and back into reservoir 44. That is, check valve 78 allows fluid to flow out of reservoir 44 and into circulation channel 48, but does not allow fluid to back flow into reservoir 44 from circulation channel 48. Check valve 78 therefore prevents reservoir 44 from ever overflowing when pump 46 is turned off and gravitational forces urge the fluid inside of hoses 30, thermal pads 32, and/or the upper regions of circulation channel 48 toward the lower regions of circulation channel 48. This helps ensure that the fluid inside of the fluid circuits does not escape into the surrounding environment, including any pathogens that may be contained within the fluid.

Figure 5:
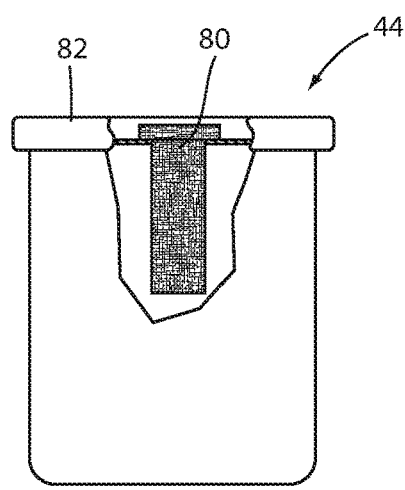
FIG. 5 is a side, elevation view of an alternative embodiment of a removable fluid reservoir that may be used with a thermal control unit, such as, but not limited to, the thermal control unit of FIG. 2.

In the embodiment shown in FIG. 3, thermal control unit 22 also includes a fluid reservoir 44 having a lid 82 with a liquid filter 80 integrated therein. Lid 82 is adapted to be selectively attachable and detachable from fluid reservoir 44. Liquid filter 80 and fluid reservoir 44 are also shown in more detail in FIG. 5. Liquid filter 80 is adapted to filter the fluid (liquid) that is poured into reservoir 44. In some embodiments, liquid filter 80 is a filter having a pore size of 0.2 microns (or otherwise constructed so as to substantially remove all particulates having a size of 0.2 microns or greater from the fluid that is poured into reservoir 44). Liquid filter 80 therefore substantially removes all bacteria from the fluid poured into reservoir 44 and helps prevent the entry and/or growth of bacteria in thermal control system 20. Further, liquid filter 80 allows ordinary tap water, rather than distilled water (or pre-filtered water) to be used with thermal control unit 22. This eliminates the expense of using distilled water and/or the time of pre-filtering water prior to pouring it into reservoir 44.

Although not shown, fluid reservoir 44 may also include an air filter integrated into lid 82, or positioned at another location on fluid reservoir 44. Such an air filter is, in some embodiments, designed to filter particulates from the air having a size greater than or equal to 0.2 microns. The air filter helps ensure that any air that is contained inside of fluid reservoir 44 is filtered prior to being released into the ambient surroundings. Such air may be released from fluid reservoir 44 due to one or more reasons. For example, when reservoir 44 is initially filled with liquid, some of the air contained therein may be forced into the surrounding atmosphere as the reservoir is filled. Alternatively, check valve 78 may allow relatively small amount of fluid to back flow into reservoir 44 prior to closing, thereby forcing small amounts of air out of reservoir 44. By including an air filter on reservoir 44, any air that is inside of reservoir 44 and forced out by the addition of liquid is directed through the air filter prior to escaping to the surrounding environment (lid 82 is adapted, in many embodiments, to provide a tight fit with the body of reservoir 44 so as to resist air leaking out of reservoir 44 via any gaps between lid 82 and the body of reservoir 44).

Figure 6:
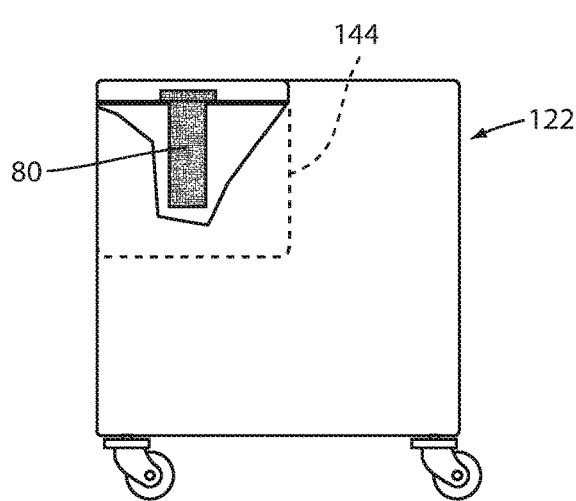
FIG. 6 is a side, elevation view of an alternative thermal control unit having an integrated fluid reservoir.

FIG. 6 illustrates an alternative embodiment of a thermal control unit 122. Thermal control unit 122 differs from thermal control unit 22 by including a built-in reservoir 144. Built-in reservoir 144, unlike reservoir 44 of thermal control unit 22, is integrated into thermal control unit 122 and not adapted to be removed for filling, emptying, and/or cleaning. Built-in reservoir 144 includes a liquid filter 80 that operates in the same manner as liquid filter 80 of reservoir 44. That is, liquid filter 80 of built-in reservoir 144 filters liquid, such as, but not limited to water, as a user pours it into built-in reservoir 144. Built-in reservoir 144 includes a removable lid 82, in some embodiments, having liquid filter 80 integrated therein. In other embodiments, built-in reservoir 144 does not include a removable lid 82. Built-in reservoir 144 may additionally include an air filter for filtering vented air, or it may only include a single combined air and liquid filter that filters incoming liquid and outgoing air.

In at least some embodiments, thermal control unit 122 is constructed such that built-in reservoir 144 is positioned to be part of the fluid circuit. That is, unlike fluid reservoir 44 whose contents are outside of the fluid circuit of thermal control unit 22, built-in reservoir 144 is constructed in some embodiments so that fluid returning from the thermal pads 32 must pass through built-in reservoir 144 before being pumped back to the thermal pads 32. In at least one of these embodiments, thermal control unit 122 is modified so that air separator 56 is incorporated into built-in reservoir 144. In such embodiments, built-in reservoir 144 includes a constricted region 72 and a plug 74 that helps ensure that the built-in reservoir 144 doesn't overflow. The constricted region 72 and plug 74 may be constructed in the same manners as previously described with respect to thermal control unit 22, or modified in order to accommodate the design of built-in reservoir 144. Further, in some embodiments of thermal control unit 122 in which built-in reservoir 144 is part of the fluid circuit and includes an air separator, fluid reservoir 144 also includes an air filter, such as air filter 60, positioned on top of the air separator in order to filter the air before being vented to the ambient surroundings.

Figure 7:
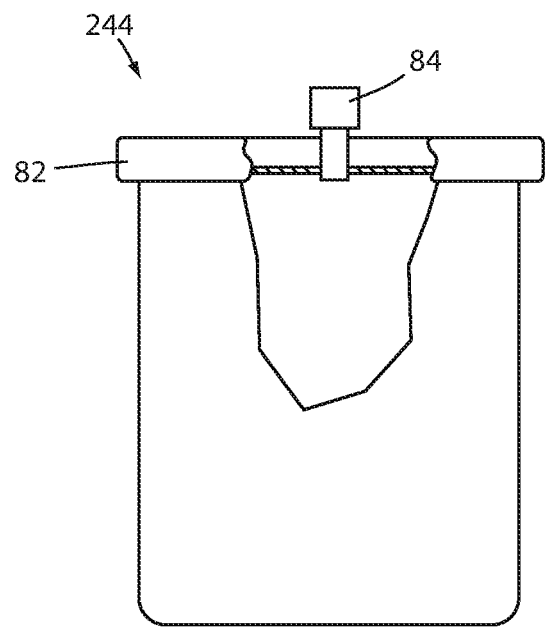
FIG. 7 is a side, elevation view of another alternative embodiment of a fluid reservoir that may be used with a thermal control unit, such as, but not limited to, the thermal control unit of FIG. 2.
Figure 8:
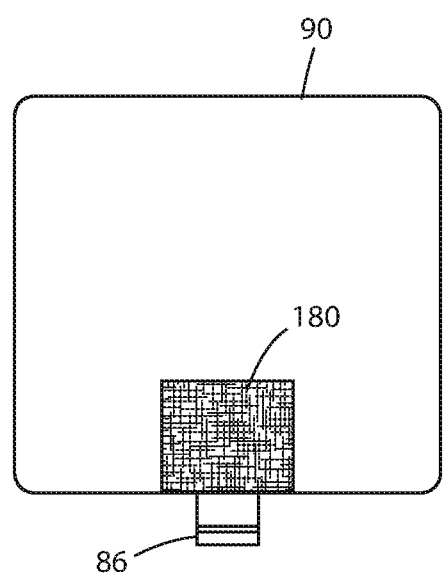
FIG. 8 is a side elevation view of a fluid container adapted to be selectively coupled to the fluid reservoir of FIG. 7.

FIGS. 7 and 8 illustrate another alternative embodiment of a fluid reservoir 244 that may be used with thermal control unit 22, or may be built-into thermal control unit 122. Fluid reservoir 244 includes a lid 82 that, in some embodiments, is not removable (or requires a special tool to remove) and that includes a fluid connector 84 integrated therein. Fluid connector 84 is adapted to mate with a second fluid connector 86 integrated into the bottom of a fluid container 90. Fluid container 90 also includes a liquid filter 180 integrated therein. Liquid filter 180 is positioned such that any fluid that escapes from fluid container 90 via second connector 86 must pass therethrough. Liquid filter 180 is adapted to filter out substantially all bacteria that may be present in the fluid contained within container 90.

Second connector 86 is adapted to prevent fluid from escaping from container 90 unless second connector 86 is engaged with connector 84 of fluid reservoir 244. That is, second connector 86 is adapted to matingly engage connector 84 and to open up when so engaged. Connector 84 is likewise adapted to open up when engaged by second connector 86 (and to remain closed when not so engaged). Connectors 84 and 86 may take on a wide variety of forms. In some embodiments, both connectors are Hansen-type quick connect couplings of the type developed by the Hansen Manufacturing Company (and now a part of Eaton Corporation of Dublin, Ireland). In other embodiments, other types of constructions of connectors 84 and 86 may be used.

Regardless of the specific construction of connectors 84 and 86, connectors 84 and 86 are adapted to help ensure that any liquid that goes inside of fluid reservoir 244 is filtered prior to entry into fluid reservoir 244. This is accomplished by making connector 84 of fluid reservoir 244 the only entry point for introducing fluid into reservoir 244. Thus, in order for a user to fill up fluid reservoir 244, the user first fills up container 90 and places container 90 on top of fluid reservoir 244 such that connector 86 engages connector 84. Once these two connectors are engaged, fluid inside of fluid container 90 is free to drain out of fluid container 90 and into fluid reservoir 244. In order for this fluid to drain into fluid reservoir 244, however, it must pass through liquid filter 180. Fluid reservoir 244 is therefore only filled with fluid that is filtered, thus reducing the likelihood of bacteria being introduced into thermal control system 20.

Although not illustrated in FIG. 7, fluid reservoir 244 may be modified to include an air filter, such as an air filter like air filter 60. Such an air filter filters air inside of fluid reservoir 244 that is displaced by the introduction of liquid into fluid reservoir 244 and vented to the ambient surroundings.

It will be understood by those skilled in the art that a number of modifications to the thermal control units 22, 122 disclosed herein may be made. For example, in some embodiments, check valve 78 is relocated from a location inside of main body 42, such as shown in FIG. 3, to a location inside of reservoir 44. In one of these embodiments, the check valve is positioned at a height such that a predefined amount of fluid may back flow into the reservoir 44 before the check valve is activated (sealed). For example, in one such embodiment, fluid reservoir 44 is constructed such that the check valve 78 is positioned generally toward the top of fluid reservoir 44, thereby allowing fluid to flow back flow into reservoir 44 until reservoir 44 reaches a threshold level that is almost full. However, once this threshold level is reached, the check valve 78 is closed, thereby preventing any more fluid from back flowing into the reservoir and thereby preventing the possibility of fluid spilling out of the reservoir 44.

In yet another embodiment, liquid filter 80 of fluid reservoir 44 may be relocated the junction between fluid reservoir 44 and valve array 62 such that the liquid inside of fluid reservoir remains unfiltered until it enters into circulating channel 48. Still other modifications are possible.

Figure 9:
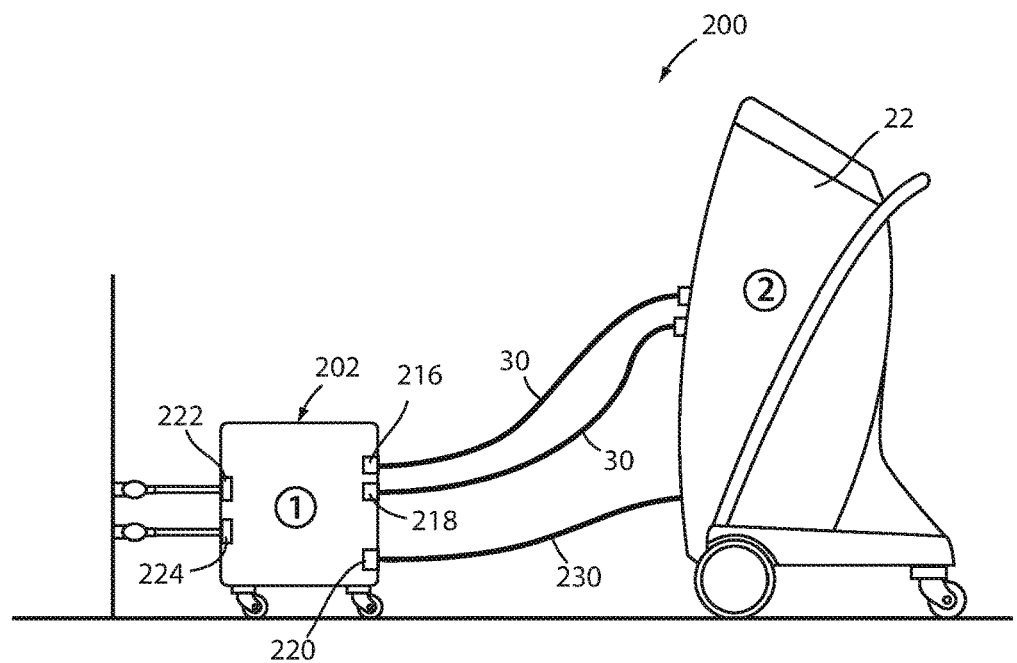
FIG. 9 is an elevation view of a thermal control unit disinfection system according to another embodiment of the present disclosure.

FIG. 9 illustrates a disinfection system 200 according to another embodiment of the present disclosure. Disinfection system 200 includes a disinfection station 202 that is adapted to disinfect one or more thermal control units, such as thermal control units 22 and/or 122. For purposes of the following description, disinfection system 200 will be described with respect to the disinfection of thermal control unit 22. However, it will be understood that disinfection system 200 can be used to disinfect thermal control unit 122, including any of the modified thermal control unit 22 and 122 discussed above. Still further, disinfection system 200 may be used to disinfect still other types of thermal control units.

Disinfection station 202 is adapted to fluidly couple to thermal control unit 22 and supply a disinfection solution to thermal control unit 22. This disinfection solution is run through the inside of thermal control unit 22 and returned back to disinfection station 202. In some situations, the user may wish to couple one or more thermal pads 32 to thermal control unit 22 during a disinfection cycle of thermal control unit 22 such that the disinfection fluid from disinfection station 202 is supplied to the pads 32 for disinfecting them. Alternatively or additionally, the user may wish to couple one or more hoses to thermal control unit 22 such that the disinfection solution from disinfection station 202 is run through the hoses during the disinfection cycle and the hoses are cleaned. In still other situations, reservoir 44 may be coupled to thermal control unit 22 during disinfection, or reservoir 44 may be removed during the disinfection cycle and disinfected manually.

Figure 10:
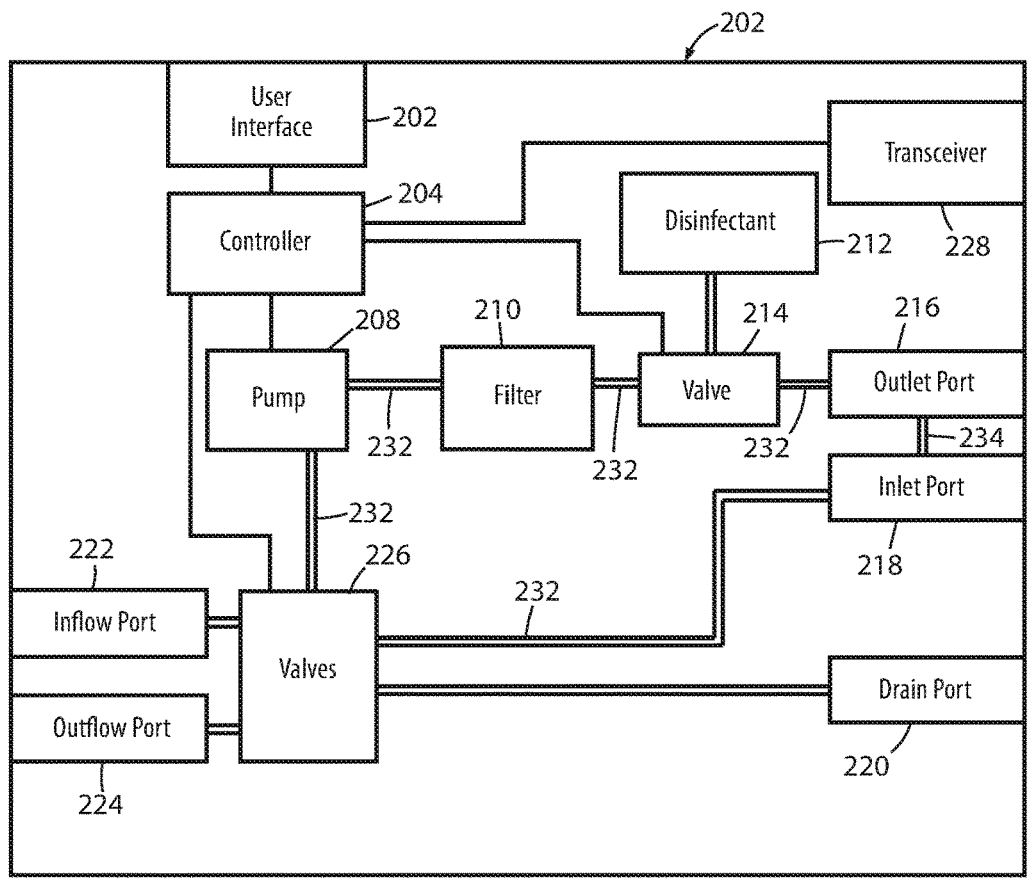
FIG. 10 is a block diagram of a disinfection station of the disinfection system of FIG. 9.

As shown more clearly in FIG. 10, disinfection station 202 includes a controller 204, a user interface 206, a pump 208, a filter 210, a disinfectant reservoir 212, a disinfectant valve 214, an outlet port 216, an inlet port 218, a drain port 220, an inflow port 222, an outflow port 224, a plurality of valves 226, and a transceiver 228. Disinfection station 202 is fluidly coupled to thermal control unit 22 by way of one or more hoses 30. Hoses 30 may be the same hoses used to couple thermal control unit 22 to a thermal pad during thermal therapy of a patient, thereby enabling the hoses 30 to be disinfected for later use when delivering thermal therapy to a patient. One of the supply lines 30a, 30b couples at one of its ends to outlet port 216 of disinfection station 202 and at the other end to one of inlets 26 on thermal control unit 22. The other of the supply lines 30a, 30b couples at one of its ends to inlet port 218 of disinfection station 202 and at its other end to one of outlets 28 of thermal control unit 22.

As shown in FIG. 9, a drain hose 230 is also coupled between disinfection station 202 and thermal control unit 22. Drain hose 230 is coupled at one of its ends to drain port 220 of disinfection station 202 and at its other end to a drain port (not shown) on thermal control unit 22. The drain port on thermal control unit 22 is positioned at any suitable location along a bottom of circulation channel 48 such that substantially all fluid within thermal control unit 22 will flow out of thermal control unit 22 through the drain port when it is opened. Such outflow of fluid is accomplished entirely by gravity in some embodiments, and in other embodiments is assisted by way of pump 46 of thermal control unit 22 and/or pump 208 of disinfection station 202. In some embodiments, the drain port is a conventional quick connector port that automatically opens when the coupling at the end of drain hose 230 is coupled thereto and automatically closes when drain hose 230 is decoupled therefrom. At least one of valves 226, which are controlled by controller 204, is coupled to drain port 220 and selectively blocks fluid from flowing into disinfection station 202 when the valve is closed, and allows fluid to flow through drain port 220 and into disinfection station 202 when the valve is open.

Controller 204 includes one or more microcontrollers suitably programmed to carry out the functions described herein, as well as other electronics for carrying out these functions, as would be known to one of ordinary skill in the art. Controller 204 may additionally, or alternatively, include one or more microprocessors, field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in disinfection station 202, or they may reside in a common location within disinfection station 202. When physically distributed, the components may communicate using any suitable serial or parallel communication protocol, such as, but not limited to, CAN, LIN, Firewire, I-squared-C, RS-232, RS-485, universal serial bus (USB), etc.

User interface 206 includes a touchscreen display in at least one embodiment. In other embodiments, other components may be included as part of user interface 206, such as, but not limited to, one or more buttons, switches, knobs, or other controls for controlling the various aspects of disinfection station 202. User interface 206 allows a user to control the operation of disinfection station 202 by communicating user commands and data to controller 204, which then uses those commands and data to control valves 226, pump 208, valve 214, and transceiver 228, as will be discussed in greater detail below.

Disinfection station 202 is utilized by appropriate personnel whenever it is desired to disinfect one or more thermal control units 22. Disinfection station 202 is used for disinfecting thermal control unit 22 by coupling a first hose 30 from outlet port 216 to one of inlets 26 on thermal control unit 22 and a second hose from inlet port 218 to one of outlets 24 on thermal control unit 22. Disinfection station 202 is also connected to a source of water, via inflow port 222. The source of water may be a conventional faucet in the healthcare facility, or it may be another source of water. In some embodiments, disinfection station 202 includes a water reservoir which is manually filled by a user. The water, in some embodiments, is distilled water, or other purified water. However, in some embodiments, regular tap water may be used that is disinfected by disinfection station 202 prior to pumping the fluid to thermal control unit 22. Outflow port 226 of disinfection station 202 is used to drain water from disinfection station 202 after the water has been used to clean thermal control unit 22. In some embodiments, outflow port 224 is coupled to a hose that has its free end coupled to the drain of a sink within the healthcare facility. Fluid flow through outflow port 224 is controlled by one or more of valves 226, which in turn are controlled by controller 204.

Prior to commencing disinfection of thermal control unit 22, a user manipulates one or more controls on user interface 206 to instruct disinfection station 202 to commence a disinfection cycle. In response to this user command, controller 204 sends instructions to transceiver 228 instructing it to establish communication with thermal control unit 22. Such communication may be wired or it may be wireless. When wired, any suitable communication protocol may be used, such as, but not limited to, a USB cable, an Ethernet cable, an RS-485 cable, or still other types of cables. When wireless, any suitable wireless communication protocol and/or technology may be used, including, but not limited to, Bluetooth, ZigBee, infrared, etc. In order to carry out such communication, thermal control unit 22 includes an appropriate transceiver within it (not shown) that is adapted to communicate with transceiver 228 of disinfection station 202. The transceiver within thermal control unit 22 is in communication with controller 40 of thermal control unit 22. The communication between transceiver 228 and the transceiver of thermal control unit 22 enables controller 204 of disinfection station 202 to communicate with the controller 40 of thermal control unit 22.

The communication between disinfection station 202 and thermal control unit 22 includes a number of commands and messages. In some embodiments, disinfection station 202 requests and receives from thermal control unit 22 a unique identifier that uniquely identifies thermal control unit 22. This unique identifier is stored in memory of disinfection station 202 and is displayable on user interface 206. Along with this identifier, controller 204 stores the time and date at which that particular thermal control unit 22 is disinfected by disinfection station 202. This data is stored for each disinfection cycle that each thermal control unit 22 undergoes. Disinfection station 202 thereby maintains a record of each time each thermal control unit 22 is disinfected. This information is displayable on user interface 206, and may be transmitted off-board disinfection station 202 to one or more other entities, such as, but not limited to, one or more servers on a local area network of the healthcare facility.

Controller 204 may be programmed, in some embodiments, to utilize the disinfection records of the thermal control units 22 to instruct appropriate personnel when it is time to clean one or more thermal control units 22, thereby relieving personnel of the task of determining when a particular thermal control unit 22 should be disinfected. In some embodiments, controller 204 transfers the disinfection record of a particular thermal control unit 22 to that particular thermal control unit 22, and a user is able to use the control panel 64 of the thermal control unit 22 to see and review the disinfection history of that particular thermal control unit 22. In such embodiments, the thermal control unit 22 may itself calculate when it next needs to be disinfected, based upon the transpired time since its previous disinfection, and/or the number and/or amount of usage since the last disinfection cycle.

In addition to the aforementioned communication, controller 204 of disinfection station 202 also tells controller 40 that a disinfection cycle is to begin, and that controller 40 should turn on its associated pump 46 and set a target fluid temperature equal to a specific temperature. The specific temperature may vary, but in some embodiments is equal to 25 degrees Celsius. Controller 40 responds to the command by controlling heat exchanger 36 in such a manner that the disinfecting solution received from disinfection station 202 has its temperature adjusted toward the commanded temperature. Controller 40 also responds by turning on pump 46 so that the disinfecting solution received from disinfection station 202 is pumped through circulation channel 48. In some embodiments, controller 204 may instruct controller 40 how long to keep pump 46 turned on and the target temperature maintained. In other embodiments, controller 204 includes a timer and monitors how long the disinfecting solution is flowing through thermal control unit 22 and, after a desired time period has elapsed, controller 204 sends a command to thermal control unit 22 instructing controller 40 to stop its pump and/or to stop using heat exchanger 36 to meet the target temperature.

In some embodiments, prior to and/or during the pumping of disinfecting fluid from disinfection station 202 to thermal control unit 22, the water inside of disinfection station 202 is disinfected by adding a suitable amount of disinfectant to the water. The disinfectant is maintained within disinfectant reservoir 212. Controller 204 controls disinfectant valve 214 in such a manner that the appropriate amount of disinfectant is added to the fluid within disinfection station 202. Once added, controller 204 closes valve 214 so that no further disinfectant is added to the fluid. In some embodiments, controller 204 operates pump 208 prior to the hoses 30 being coupled to thermal control unit 22. The operation of pump 208 causes fluid to flow internally within a circulation channel 232 inside of disinfection station 202. Circulation channel 232 flows through pump 208, filter 210, valve 214, outlet port 216, a bypass 234, inlet port 218, valves 226, and back to pump 208. Bypass line 234 may include a valve that is operated by controller 204 and that opens when fluid is to be pumped internally within disinfection station 202 and that closes when fluid is pumped externally from outlet port 216 to thermal control unit 22.

In other embodiments, pump 208 need not be operated prior to coupling disinfection station 202 to thermal control unit 22. In such embodiments, disinfectant may be added to the water at the same time it is being pumped out of outlet port 216 to thermal control unit 22. Further, in such embodiments, bypass line 234 may be omitted, if desired.

During disinfection of thermal control unit 22, water with disinfectant added to it (disinfecting solution) is pumped from outlet port 216 to one of inlets 26 of thermal control unit 22. The disinfecting solution then flows through the inlet 26 port of thermal control unit 22 into return manifold 34. From return manifold 34, the disinfecting solution is pumped along the entire circulation channel 48 of thermal control unit 22 until the fluid reaches outlet manifold 38. From there, a portion of the disinfecting solution passes through bypass line 52 and returns back to return manifold 34. The rest of the disinfecting solution within outlet manifold 38 is pumped through one of the outlets 24 to a hose 30 that is coupled at its other end to disinfecting station 202. The fluid then returns to disinfecting station 202 and, in some embodiments, passes again through circulation channel 232 of disinfection station 202 (where additional disinfectant may be added from reservoir 212) before being pumped back to thermal control unit 22. In other embodiments, the disinfecting fluid that returns from thermal control unit 22 is diverted to outflow port 224 and discarded.

In other embodiments, rather than having disinfecting solution flow back and forth between thermal control unit 22 and disinfection station 202, the disinfecting solution is initially pumped to thermal control unit 22 and remains within thermal control unit 22 until the disinfection time has expired. In these embodiments, a hose 30 coupling one of outlet 24 to disinfection station 202 may be omitted and the return of the disinfecting solution from thermal control unit 22 to disinfection station 202 may be accomplished via drain hose 230. Alternatively, one or more valves may be included in thermal control unit 22 that selectively allow and disallow fluid to exit from thermal control unit 22 via outlet 24. When so included, controller 40 of thermal control unit 22 keeps such valves closed during the disinfection cycle. After the disinfecting solution has been pumped internally within circulation channel 48 of thermal control unit 22 for the desired amount of time, controller 48 opens up one or more of the valves controlling outlet 24. The opening up of one or more of these valves allows fluid to flow out of the outlet 24 and back to disinfecting station 202.

In sum, the supply of disinfecting solution to thermal control unit 22 may be implemented in any of at least the three following manners and/or combinations thereof: (1) pumping disinfecting fluid in a fluid circuit that includes both disinfection station 202 and thermal control unit 22 for a designated time period; (2) pumping disinfecting fluid to thermal control unit 22 where it is pumped and maintained internally within thermal control unit 22 for a designated time period and then returned to disinfection station 202 for drainage via outflow port 224; and/or (3) pumping fluid from inflow port 222 of disinfection station 202 to thermal control unit 22, circulating it therein, and returning it to disinfection station 202 where it is discarded via outflow port 224. In the third manner, fresh fluid is continually supplied to disinfection station 202 via inflow port 222 during the disinfection period, and the disinfection solution fluid that returns to disinfection station 202 from thermal control unit 22 is continuously discarded via outflow port 224.

Regardless of the specific manner in which disinfecting solution is supplied to and circulated through thermal control unit 22, the flow of disinfecting solution through thermal control unit 22 continues for a predetermined amount of time. After the predetermined time period expires, the disinfecting solution within thermal control unit 22 is drained therefrom by opening one or more valves 226 associated with drain port 220, thereby enabling the fluid within thermal control unit 22 to drain out to disinfecting station 202 via drain hose 230. The drained fluid is discarded by disinfecting station 202 via outflow port 224.

After the disinfecting solution has been drained from thermal control unit 22 and disinfection station 202, the disinfection cycle of thermal control unit 22 may also include a rinse cycle. During the rinse cycle, fresh fluid is supplied to disinfection station 202 via inflow port 222, or manually from a user, or from a fluid reservoir (not shown) contained within disinfecting station 202. The fresh fluid is pumped to thermal control unit 22 without the addition of any disinfectant from reservoir 212 (or with a reduced amount of disinfectant, or with a different disinfectant or additive added thereto). The fresh fluid is then circulated through thermal control unit for a designated rinse time. The designated rinse time may be the same as the designated time during which disinfecting solution was previously circulated through thermal control unit 22, or it may be for a different amount of time. The supply and circulation of fresh fluid to thermal control unit 22 during the rinse cycle may be accomplished in any of the three different manner described above for supplying and circulating disinfecting solution through thermal control unit 22. That is, the rinsing fluid may be pumped back and forth in a circuit that includes disinfecting station 202 and thermal control unit 22; may be pumped to thermal control unit 22 and maintained therein during the entire rinse cycle; and/or may be continuously supplied via port 222, pumped to thermal control unit 22 for rinsing, and continuously drained via outflow port 224 after being received back from thermal control unit 22.

After the rinse cycle has ended, any remaining fluid within thermal control unit 22 is drained via drain hose 230. The drained fluid is returned to disinfection station 202, which discards the fluid via outflow port 224. In some embodiments, multiple disinfection and/or rinse cycles may be implemented, while in other embodiments, only a single disinfection cycle and rinse cycle is used to clean a thermal control unit 22. After the rinse cycle is completed, in some embodiments, disinfection station 202 supplies an amount of clean fluid to thermal control unit 22 sufficient to enable thermal control unit 22 to be used for thermally treating a patient. In this manner, a user does not need to manually fill reservoir 44 with fluid to prepare thermal control unit 22 for use with a patient. Instead, disinfection station 202 automatically prepares thermal control unit 22 for use. In still other embodiments, a user can instruct disinfection station 202 via user interface 206 whether or not to fill thermal control unit 22 with thermal fluid after the rinse cycle is complete. Still further, in some embodiments, controller 204 and/or controller 40 record the time at which the rinse cycle was completed, store that time in memory, and make it available for later viewing by a user and/or for transmission to another electronic device.

Thermal control unit 22 includes a plurality of inlets 26 and a plurality of outlets 24. As was described above, when thermal control unit 22 is to be disinfected, a hose 30 is coupled to one of the inlets 26 and a hose 30 is coupled to one of the outlets 24. In order to disinfect those inlets and outlets to which no hose 30 is coupled, a user may connect one or more additional hoses to outlets 24 and inlets 26. One such hose may have its first end coupled to an outlet 24 and its other end to an inlet 26. Another hose may similarly have its first end coupled to another one of the outlets 24 and its other end to another one of the inlets 26. The addition of these hoses allows disinfecting fluid and rinsing fluid to flow through the outlets 24 and back through the inlets 26 during the disinfection and rinsing cycles, thereby ensuring that all of the inlets 26 and outlets 24 are disinfected and rinsed during these cycles.

In some embodiments, disinfecting station 202 is modified to include only one port for coupling a hose between disinfection station 202 and thermal control unit 22, such as drain port 220. In these modified embodiments, disinfecting station 202 initially supplies disinfecting solution to thermal control unit 22 by pumping the disinfecting solution out drain port 220 and through drain hose 230 to thermal control unit 22. Once inside thermal control unit 22, the disinfecting solution is pumped by pump 46 through circulation channel 48 for the prescribed amount of time. When the prescribed time has expired, the disinfecting solution is drained from thermal control unit 22 via drain hose 30 and discarded out outflow port 224 of disinfecting station 202. Thereafter, a rinse cycle is completed in the same way, utilizing drain hose 30 to supply thermal control unit 22 with rinsing fluid and to thereafter drain away the rinsing fluid when the rinsing cycle is complete.

As shown in FIG. 10, disinfecting station 202 includes a filter 210 that filters pollutants from the fluid circulating through disinfecting station 202. Filter 210 may be a 0.2 micron filter adapted to filter out pollutants having a size greater than 0.2 microns. Alternatively, filter 210 may be adapted to filter pollutants having a different size. Filter 210 may also, or alternatively, be a set of filters that work together to ensure that the fluid supplied to thermal control unit 22 is appropriately filtered. In some embodiments, filter 210 is constructed in accordance with any of the filter arrangements disclosed in commonly assigned U.S. patent application Ser. No. 62/406,676 filed Oct. 11, 2016, by inventors Marko Kostic et al. and entitled THERMAL CONTROL SYSTEM, the complete disclosure of which is incorporated herein by reference. In other embodiments, filter 210 is constructed in different manners.

By including filter 210 within disinfection station 202, it is possible to modify thermal control unit 22 so that it omits one or more of filters 54, 60, and 80. That is, through the regular disinfection of the thermal control unit 22 using disinfection station 202, it may not be necessary or desirable to use one or more filters contained within thermal control unit 22. The filtering performed by such filters can be effectively replaced with the filtering action of filter 210 during the disinfection cycles of the modified thermal control unit 22. In other words, the thermal control units can be maintained in a clean state by the periodic usage of disinfection station 202. Thus, disinfection station 202 can be used as a replacement for one or more of filters 54, 60, and/or 80. Alternatively, disinfection station 202 can be used as a supplement to these filters whereby the thermal control units include their own filters in addition to filter 210 of disinfection station 202.

Disinfection station 202 may be modified to include multiple outlet ports 216 and inlet ports 218. When such multiple inlet and outlet ports are included, disinfection station 202 is able to simultaneously disinfect multiple thermal control units 22. Hoses 30 are coupled between the multiple thermal control units 22 and the multiple pairs of inlet and outlet ports 218 and 216. Disinfecting solution is then pumped from disinfecting station 202 to each thermal control unit 22. In one such embodiment, the multiple thermal control units 22 are coupled to disinfecting station 202 in parallel, rather than in series, such that the disinfecting solution exiting a particular thermal control unit 22 returns directly back to disinfection station 202 rather than being pumped to another thermal control unit 22 before returning to disinfection station 202.

User interface 206 is configured in some embodiments of disinfecting station 202 to automatically carry out the entire disinfecting and rinse cycles for a thermal control unit 22 upon pressing a single button on user interface 206, or otherwise activating a single control on user interface 206.

In this manner, a user merely needs to couple the requisite hoses between thermal control unit 22 and disinfecting station 202 and activate the single control. Thereafter, the user does not need to participate in the disinfection cycle and/or rinse cycle. Still further, the user does not need to manually drain either the thermal control unit 22 or the disinfecting station 202. All of these tasks are accomplished automatically under the control of controller 204 in response to the activation of the single control.

Disinfection station 202 may be adapted, in some embodiments, to disinfect different models and/or types of thermal control units 22. In such embodiments, disinfection station 202 can be modified to implement disinfecting and rinsing cycles of different durations, different target temperatures, and/or of other different variables in order to match the particular thermal control unit 22 being disinfected by disinfection station 202. Information identifying the particular thermal control unit 22 to be disinfected may be passed automatically from the controller of the thermal control unit 22 to transceiver 228, or it may be manually entered by a user into disinfection station 202 using user interface 206. As a result, controller 204 of disinfection unit 202 makes appropriate adjustments to the disinfection and/or rinsing cycle associated with that particular thermal control unit 22.

Disinfection station 202 may be adapted to utilize any of the disinfection solutions and/or disinfection techniques disclosed in commonly assigned U.S. patent application Ser. No. 15/611,048 filed Jun. 1, 2017, by inventors Matthew Ward et al. and entitled METHOD OF DISINFECTING A THERMAL CONTROL UNIT, the complete disclosure of which is incorporated herein by reference.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit comprising:
    a fluid circuit having a fluid outlet adapted to couple to a fluid supply line and a fluid inlet adapted to couple to a fluid return line;
    a reservoir for supplying a liquid to the fluid circuit, the reservoir positioned outside of the fluid circuit such that fluid returning from the fluid return line is pumped back to the fluid supply line without passing through the reservoir;
    a heat exchanger in the fluid circuit and adapted to change a temperature of the liquid in the fluid circuit;
    a pump for circulating the liquid supplied by the reservoir through the fluid circuit;
    a liquid filter coupleable to the reservoir, the liquid filter positioned such that filling the reservoir with the liquid requires passing the liquid through the liquid filter when the liquid filter is coupled to the reservoir;
    an air eliminator for venting air from the fluid circuit to the ambient surroundings;
    a first air filter coupled to the air eliminator, the first air filter adapted to filter particulates from the air vented to the ambient surroundings;
    a second air filter coupled to the reservoir, the reservoir being fluidly sealed from the ambient surroundings except at a location of the second air filter, the second air filter adapted to filter particulates from air vented out of the reservoir to the ambient surroundings; and
    a controller adapted to control the heat exchanger such that a temperature of the circulating liquid is adjustable toward a desired temperature.

2. The thermal control unit of claim 1, wherein the air eliminator includes a plug having a position that varies in response to a level of the liquid in the thermal control unit, the plug adapted to fluidly isolate the first air filter from the liquid in the thermal control unit if the level of the liquid in the thermal control unit exceeds a threshold.

3. The thermal control unit of claim 2, wherein the plug floats in the liquid.

4. The thermal control unit of claim 3, wherein the plug rises and falls with rising and falling levels of the liquid in the thermal control unit.

5. The thermal control unit of claim 4, wherein the plug sealingly engages an aperture when the plug rises past a threshold height, the aperture being positioned between the first air filter and the liquid.

6. The thermal control unit of claim 1, wherein the first air filter has a pore size adapted to filter out particles of 0.2 microns or larger.

7. The thermal control unit of claim 1, wherein the second air filter has a pore size adapted to filter out particles of 0.2 microns or larger.

8. The thermal control unit of claim 1, further including a check valve positioned between the reservoir and the fluid circuit, the check valve adapted to prevent the liquid from flowing out of the fluid circuit and into the reservoir.

9. The thermal control unit of claim 1, wherein the liquid filter is integrated into a removable lid adapted to be selectively attached to, and detached from, the reservoir.

10. The thermal control unit of claim 9, wherein the reservoir is adapted to be lifted out of the thermal control unit without leaking the liquid.

11. A thermal control unit comprising:
    a fluid circuit having a fluid outlet adapted to couple to a fluid supply line and a fluid inlet adapted to couple to a fluid return line;
    a reservoir for supplying a liquid to the fluid circuit;
    a heat exchanger in the fluid circuit and adapted to change a temperature of the liquid in the fluid circuit;
    a pump for circulating the liquid supplied by the reservoir through the fluid circuit;
    a combined air and liquid filter coupled to the reservoir, the combined air and liquid filter adapted to filter liquid poured into the reservoir and to filter air escaping from the reservoir;
    an air eliminator for venting air from the fluid circuit to the ambient surroundings, the air eliminator including an air filter and a plug having a position that varies in response to a level of the liquid in the thermal control unit, the air filter adapted to filter particulates from air passing through the air filter, and the plug adapted to fluidly isolate the air filter from the liquid in the thermal control unit if the level of the liquid in the thermal control unit exceeds a threshold; and a controller adapted to control the heat exchanger such that a temperature of the circulating liquid is adjustable toward a desired temperature.

12. The thermal control unit of claim 11, wherein the plug rises and falls with rising and falling levels of the liquid in the thermal control unit, and the plug sealingly engages an aperture when the plug rises past a threshold height, the aperture being positioned between the air filter and the liquid.

13. The thermal control unit of claim 12, further including a check valve positioned between the reservoir and the fluid circuit, the check valve adapted to prevent the liquid from flowing out of the fluid circuit and into the reservoir.

14. The thermal control unit of claim 11, wherein the combined air and liquid filter is integrated into a removable lid adapted to be selectively attached to, and detached from, the reservoir.

* * * * *